(12) United States Patent
Araujo et al.

(10) Patent No.: US 11,881,721 B2
(45) Date of Patent: Jan. 23, 2024

(54) WIRELESS ENERGY TRANSFER SYSTEM WITH FAULT DETECTION

(71) Applicant: KARDION GMBH, Stuttgart (DE)

(72) Inventors: Samuel Vasconcelos Araujo, Esslingen (DE); Michael Jiptner, Besigheim (DE)

(73) Assignee: Kardion GmbH, Stuttgart (DE)

( * ) Notice: Subject to any disclaimer, the term of this patent is extended or adjusted under 35 U.S.C. 154(b) by 31 days.

(21) Appl. No.: 17/051,401

(22) PCT Filed: May 2, 2019

(86) PCT No.: PCT/EP2019/061294
§ 371 (c)(1),
(2) Date: Jun. 28, 2021

(87) PCT Pub. No.: WO2019/211400
PCT Pub. Date: Nov. 7, 2019

(65) Prior Publication Data
US 2021/0351628 A1 Nov. 11, 2021

(30) Foreign Application Priority Data
May 2, 2018 (DE) .......................... 102018206724.4

(51) Int. Cl.
*H02J 50/00* (2016.01)
*H02J 50/12* (2016.01)
(Continued)

(52) U.S. Cl.
CPC ............ *H02J 50/12* (2016.02); *A61N 1/3787* (2013.01); *H02J 7/007* (2013.01); *H02J 7/0029* (2013.01);
(Continued)

(58) Field of Classification Search
CPC .................................. H02J 50/00; H04B 5/00
See application file for complete search history.

(56) References Cited

U.S. PATENT DOCUMENTS 2,254,698 A 9/1941 Hansen, Jr.
3,085,407 A 4/1963 Tomlinson
(Continued)

FOREIGN PATENT DOCUMENTS

CA 3 000 581 4/2017
CN 103143072 6/2013
(Continued)

OTHER PUBLICATIONS

International Search Report and Written Opinion received in PCT Application No. PCT/EP2019/061294, dated Jun. 14, 2019 in 11 pages.
(Continued)

*Primary Examiner* — Adi Amrany
(74) *Attorney, Agent, or Firm* — Knobbe, Martens, Olson & Bear, LLP

(57) ABSTRACT

The invention relates to an energy transfer system for the wireless transfer of energy, having a transmitter unit and a receiver unit separate therefrom, wherein the transmitter unit has a primary coil that is able to be supplied with a supply voltage, and wherein the receiver unit has a secondary coil to which an energy sink is connected via a rectifier, wherein the receiver unit is configured so as to detect a fault case in an energy flow from the secondary coil to the energy sink and, in the fault case, to execute a fault mode (F) having at least one operating parameter ($I_{out}$) of the receiver unit that is preferably in a range outside the given specification (B), and in that the transmitter unit is configured so as to recognize the fault mode (F) of the receiver unit and to perform a fault response (N) in response.

19 Claims, 2 Drawing Sheets

(51) Int. Cl.
*H02J 50/10* (2016.01)
*H02J 50/70* (2016.01)
*A61N 1/378* (2006.01)
*H02J 7/00* (2006.01)
*H02J 50/80* (2016.01)
*H02J 7/02* (2016.01)

(52) U.S. Cl.
CPC .............. *H02J 7/0047* (2013.01); *H02J 7/02* (2013.01); *H02J 50/10* (2016.02); *H02J 50/70* (2016.02); *H02J 50/80* (2016.02); *H02J 7/00034* (2020.01); *H02J 7/0048* (2020.01)

(56) References Cited

U.S. PATENT DOCUMENTS

| | | | |
|---|---|---|---|
| 3,614,181 | A | 10/1971 | Meeks |
| 3,645,268 | A | 2/1972 | Capote |
| 3,747,998 | A | 7/1973 | Klein et al. |
| 3,807,813 | A | 4/1974 | Milligan |
| 4,441,210 | A | 4/1984 | Hochmair et al. |
| 4,888,009 | A | 12/1989 | Lederman et al. |
| 4,888,011 | A | 12/1989 | Kung et al. |
| 4,896,754 | A | 1/1990 | Carlson et al. |
| 5,000,177 | A | 3/1991 | Hoffmann et al. |
| 5,195,877 | A | 3/1993 | Kletschka |
| 5,289,821 | A | 3/1994 | Swartz |
| 5,443,503 | A | 8/1995 | Yamane |
| 5,599,173 | A | 2/1997 | Chen et al. |
| 5,613,935 | A | 3/1997 | Jarvik |
| 5,629,661 | A | 5/1997 | Ooi et al. |
| 5,690,674 | A | 11/1997 | Diaz |
| 5,713,954 | A | 2/1998 | Rosenberg et al. |
| 5,766,207 | A | 6/1998 | Potter et al. |
| 5,843,141 | A | 12/1998 | Bischoff et al. |
| 5,888,242 | A | 3/1999 | Antaki et al. |
| 6,058,958 | A | 5/2000 | Benkowski et al. |
| 6,149,405 | A | 11/2000 | Abe et al. |
| 6,212,430 | B1 | 4/2001 | Kung et al. |
| 6,224,540 | B1 | 5/2001 | Lederman et al. |
| 6,254,359 | B1 | 7/2001 | Aber |
| 6,264,601 | B1 | 7/2001 | Jassawalla et al. |
| 6,324,430 | B1 | 11/2001 | Zarinetchi et al. |
| 6,324,431 | B1 | 11/2001 | Zarinetchi et al. |
| 6,361,292 | B1 | 3/2002 | Chang et al. |
| 6,366,817 | B1 | 4/2002 | Kung |
| 6,389,318 | B1 | 5/2002 | Zarinetchi et al. |
| 6,398,734 | B1 | 6/2002 | Cimochowski et al. |
| 6,400,991 | B1 | 6/2002 | Kung |
| 6,442,434 | B1 | 8/2002 | Zarinetchi et al. |
| 6,445,956 | B1 | 9/2002 | Laird et al. |
| 6,471,713 | B1 | 10/2002 | Vargas et al. |
| 6,496,733 | B2 | 12/2002 | Zarinetchi et al. |
| 6,508,756 | B1 | 1/2003 | Kung et al. |
| 6,527,698 | B1 | 3/2003 | Kung et al. |
| 6,530,876 | B1 | 3/2003 | Spence |
| 6,540,658 | B1 | 4/2003 | Fasciano et al. |
| 6,561,975 | B1 | 5/2003 | Pool et al. |
| 6,592,620 | B1 | 7/2003 | Lancisi et al. |
| 6,979,338 | B1 | 12/2005 | Loshakove et al. |
| 7,062,331 | B2 | 6/2006 | Zarinetchi et al. |
| 7,070,398 | B2 | 7/2006 | Olsen et al. |
| 7,155,291 | B2 | 12/2006 | Zarinetchi et al. |
| 7,160,243 | B2 | 1/2007 | Medvedev |
| 7,338,521 | B2 | 3/2008 | Antaki et al. |
| 7,513,864 | B2 | 4/2009 | Kantrowitz et al. |
| 7,520,850 | B2 | 4/2009 | Brockway |
| 7,762,941 | B2 | 7/2010 | Jarvik |
| 7,794,384 | B2 | 9/2010 | Sugiura et al. |
| 7,819,916 | B2 | 10/2010 | Yaegashi |
| 7,942,805 | B2 | 5/2011 | Shambaugh, Jr. |
| 7,959,551 | B2 | 6/2011 | Jarvik |
| 8,012,079 | B2 | 9/2011 | Delgado, III |
| 8,075,472 | B2 | 12/2011 | Zilbershlag et al. |
| 8,088,059 | B2 | 1/2012 | Jarvik |
| 8,231,519 | B2 | 7/2012 | Reichenbach et al. |
| 8,489,200 | B2 | 7/2013 | Zarinetchi et al. |
| 8,608,635 | B2 | 12/2013 | Yomtov et al. |
| 8,612,002 | B2 | 12/2013 | Faltys et al. |
| 8,620,447 | B2 | 12/2013 | D'Ambrosio et al. |
| 8,766,788 | B2 | 7/2014 | D'Ambrosio |
| 8,827,890 | B2 | 9/2014 | Lee et al. |
| 8,862,232 | B2 | 10/2014 | Zarinetchi et al. |
| 8,870,739 | B2 | 10/2014 | LaRose et al. |
| 8,900,114 | B2 | 12/2014 | Tansley et al. |
| 8,961,389 | B2 | 2/2015 | Zilbershlag |
| 9,002,468 | B2 | 4/2015 | Shea et al. |
| 9,002,469 | B2 | 4/2015 | D'Ambrosio |
| 9,071,182 | B2 | 6/2015 | Yoshida et al. |
| 9,220,826 | B2 | 12/2015 | D'Ambrosio |
| 9,283,314 | B2 | 3/2016 | Prasad et al. |
| 9,381,286 | B2 | 7/2016 | Spence et al. |
| 9,440,013 | B2 | 9/2016 | Dowling et al. |
| 9,456,898 | B2 | 10/2016 | Barnes et al. |
| 9,486,566 | B2 | 11/2016 | Siess |
| 9,492,600 | B2 | 11/2016 | Strueber et al. |
| 9,539,094 | B2 | 1/2017 | Dale et al. |
| 9,561,362 | B2 | 2/2017 | Malinowski |
| 9,569,985 | B2 | 2/2017 | Alkhatib et al. |
| 9,592,397 | B2 | 3/2017 | Hansen et al. |
| 9,603,984 | B2 | 3/2017 | Romero et al. |
| 9,616,107 | B2 | 4/2017 | VanAntwerp et al. |
| 9,713,701 | B2 | 7/2017 | Sarkar et al. |
| 9,717,831 | B2 | 8/2017 | Schuermann |
| 9,724,083 | B2 | 8/2017 | Quadri et al. |
| 9,800,172 | B1 * | 10/2017 | Leabman ............... H02M 7/217 |
| 9,833,314 | B2 | 12/2017 | Corbett |
| 9,833,611 | B2 | 12/2017 | Govea et al. |
| 9,848,899 | B2 | 12/2017 | Sliwa et al. |
| 10,143,571 | B2 | 12/2018 | Spence et al. |
| 10,463,508 | B2 | 11/2019 | Spence et al. |
| 11,000,282 | B2 | 5/2021 | Schuelke et al. |
| 11,056,878 | B2 * | 7/2021 | Gao ....................... H02M 7/217 |
| 11,065,437 | B2 | 7/2021 | Aber et al. |
| 11,103,715 | B2 | 8/2021 | Fort |
| 11,110,265 | B2 | 9/2021 | Johnson |
| 11,179,559 | B2 | 11/2021 | Hansen |
| 11,224,737 | B2 | 1/2022 | Petersen et al. |
| 11,291,826 | B2 | 4/2022 | Tuval et al. |
| 11,317,988 | B2 | 5/2022 | Hansen et al. |
| 11,344,717 | B2 | 5/2022 | Kallenbach et al. |
| 11,351,359 | B2 | 6/2022 | Clifton et al. |
| 11,351,360 | B2 | 6/2022 | Rudser et al. |
| 11,368,081 | B2 | 6/2022 | Vogt et al. |
| 11,406,483 | B2 | 8/2022 | Wirbisky et al. |
| 11,406,520 | B2 | 8/2022 | Lam |
| 11,406,802 | B2 | 8/2022 | DeGraaf et al. |
| 11,413,443 | B2 | 8/2022 | Hodges et al. |
| 11,413,444 | B2 | 8/2022 | Nix et al. |
| 11,439,806 | B2 | 9/2022 | Kimball et al. |
| 11,471,692 | B2 | 10/2022 | Aghassian et al. |
| 11,517,737 | B2 | 12/2022 | Struthers et al. |
| 11,517,740 | B2 | 12/2022 | Agarwa et al. |
| 11,529,508 | B2 | 12/2022 | Jablonsk et al. |
| 11,583,671 | B2 | 2/2023 | Nguyen et al. |
| 11,596,727 | B2 | 3/2023 | Siess et al. |
| 11,699,551 | B2 | 7/2023 | Diekhans et al. |
| 2002/0177324 | A1 | 11/2002 | Metzler |
| 2003/0040765 | A1 | 2/2003 | Breznock |
| 2003/0125766 | A1 | 7/2003 | Ding |
| 2003/0130581 | A1 | 7/2003 | Salo et al. |
| 2004/0167410 | A1 | 8/2004 | Hettrick |
| 2005/0006083 | A1 | 1/2005 | Chen et al. |
| 2005/0107847 | A1 | 5/2005 | Gruber et al. |
| 2006/0004423 | A1 | 1/2006 | Boveja et al. |
| 2006/0190036 | A1 | 8/2006 | Wendel et al. |
| 2006/0196277 | A1 | 9/2006 | Allen et al. |
| 2007/0129767 | A1 | 6/2007 | Wahlstrand |
| 2007/0282209 | A1 | 12/2007 | Lui et al. |
| 2008/0015481 | A1 | 1/2008 | Bergin et al. |
| 2008/0079392 | A1 * | 4/2008 | Baarman ............... H02J 7/0072 320/108 |
| 2008/0082005 | A1 | 4/2008 | Stern et al. |
| 2008/0266922 | A1 | 10/2008 | Mumtaz et al. |

(56) References Cited

U.S. PATENT DOCUMENTS

| | | |
|---|---|---|
| 2009/0010462 A1 | 1/2009 | Ekchian et al. |
| 2009/0024042 A1 | 1/2009 | Nunez et al. |
| 2009/0198307 A1 | 8/2009 | Mi et al. |
| 2009/0198312 A1 | 8/2009 | Barker |
| 2009/0276016 A1 | 11/2009 | Phillips et al. |
| 2009/0312650 A1 | 12/2009 | Maile et al. |
| 2010/0191035 A1 | 7/2010 | Kang et al. |
| 2010/0331918 A1 | 12/2010 | Digiore et al. |
| 2011/0137394 A1 | 6/2011 | Lunsford et al. |
| 2011/0224720 A1 | 9/2011 | Kassab et al. |
| 2012/0022645 A1 | 1/2012 | Burke |
| 2012/0050931 A1* | 3/2012 | Terry ............... H02J 7/025 361/91.1 |
| 2012/0158074 A1 | 6/2012 | Hall |
| 2013/0099585 A1* | 4/2013 | Von Novak ......... H04B 5/0031 307/104 |
| 2013/0116575 A1 | 5/2013 | Mickle et al. |
| 2013/0303970 A1 | 11/2013 | Keenan et al. |
| 2014/0012282 A1 | 1/2014 | Fritsch |
| 2014/0039587 A1 | 2/2014 | Romero |
| 2014/0063666 A1* | 3/2014 | Kallal ............... H02J 50/27 361/56 |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0233184 A1 | 8/2014 | Thompson et al. |
| 2014/0265620 A1 | 9/2014 | Hoarau et al. |
| 2015/0028805 A1 | 1/2015 | Dearden et al. |
| 2015/0090372 A1 | 4/2015 | Branagan et al. |
| 2015/0196076 A1 | 7/2015 | Billingslea |
| 2015/0290372 A1 | 10/2015 | Muller et al. |
| 2015/0290373 A1 | 10/2015 | Rudser et al. |
| 2015/0333532 A1 | 11/2015 | Han et al. |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0175501 A1 | 6/2016 | Schuermann |
| 2016/0268846 A1 | 9/2016 | Akuzawa et al. |
| 2016/0271309 A1 | 9/2016 | Throckmorton et al. |
| 2016/0331980 A1 | 11/2016 | Strommer et al. |
| 2016/0344302 A1* | 11/2016 | Inoue ............... H02M 7/219 |
| 2017/0047781 A1* | 2/2017 | Stanislawski ....... H02J 7/00034 |
| 2017/0070082 A1 | 3/2017 | Zheng et al. |
| 2017/0136164 A1 | 5/2017 | Yeatts |
| 2017/0143977 A1 | 5/2017 | Kaib et al. |
| 2017/0203104 A1 | 7/2017 | Nageri et al. |
| 2017/0231717 A1 | 8/2017 | Forsell |
| 2017/0271919 A1* | 9/2017 | Von Novak, III ...... H02J 50/15 |
| 2017/0275799 A1 | 9/2017 | Chen |
| 2017/0288448 A1 | 10/2017 | Kranz et al. |
| 2017/0353053 A1* | 12/2017 | Muratov ............ H02J 50/12 |
| 2017/0354812 A1 | 12/2017 | Callaghan et al. |
| 2018/0078329 A1 | 3/2018 | Hansen et al. |
| 2018/0207336 A1 | 7/2018 | Solem |
| 2018/0256796 A1 | 9/2018 | Hansen |
| 2018/0256800 A1 | 9/2018 | Conyers et al. |
| 2018/0280708 A1 | 10/2018 | Escalona et al. |
| 2019/0004037 A1 | 1/2019 | Zhang et al. |
| 2019/0060543 A1 | 2/2019 | Khanal et al. |
| 2019/0068004 A1* | 2/2019 | Louis ............... H02J 50/12 |
| 2019/0097447 A1* | 3/2019 | Partovi ............. H02J 7/025 |
| 2019/0175808 A1 | 6/2019 | Zilbershlag et al. |
| 2019/0222064 A1* | 7/2019 | Du ................. H02H 7/1227 |
| 2019/0344000 A1 | 11/2019 | Kushwaha et al. |
| 2019/0351120 A1 | 11/2019 | Kushwaha et al. |
| 2019/0393735 A1* | 12/2019 | Lee ................. H02J 50/12 |
| 2020/0054806 A1 | 2/2020 | Sun |
| 2020/0139032 A1 | 5/2020 | Bryson et al. |
| 2020/0227954 A1 | 7/2020 | Ding et al. |
| 2020/0350812 A1 | 11/2020 | Vogt et al. |
| 2021/0052793 A1 | 2/2021 | Struthers et al. |
| 2021/0057804 A1 | 2/2021 | Wenning |
| 2021/0143688 A1* | 5/2021 | Agrawal ............ H02J 50/80 |
| 2021/0290931 A1 | 9/2021 | Baumbach |
| 2021/0322011 A1 | 10/2021 | Schuelke et al. |
| 2021/0336484 A1 | 10/2021 | Araujo et al. |
| 2021/0339009 A1 | 11/2021 | Stotz et al. |
| 2021/0379360 A1 | 12/2021 | Schellenberg |
| 2021/0386990 A1 | 12/2021 | Stotz et al. |
| 2021/0393944 A1 | 12/2021 | Wenning |
| 2021/0399582 A1 | 12/2021 | Araujo et al. |
| 2022/0080184 A1 | 3/2022 | Clifton et al. |
| 2022/0080185 A1 | 3/2022 | Clifton et al. |
| 2022/0139614 A1 | 5/2022 | Diekhans et al. |
| 2022/0320901 A1 | 10/2022 | Araujo et al. |
| 2022/0407403 A1 | 12/2022 | Vogt et al. |
| 2023/0191141 A1 | 6/2023 | Wenning et al. |

FOREIGN PATENT DOCUMENTS

| | | |
|---|---|---|
| CN | 103942511 | 7/2014 |
| CN | 104274873 | 1/2015 |
| CN | 104888293 | 3/2017 |
| CN | 106776441 | 5/2017 |
| DE | 103 02 550 | 8/2004 |
| DE | 10 2012 200 912 | 7/2013 |
| DE | 11 2012 005 944 | 12/2014 |
| DE | 10 2016 106 683 | 10/2016 |
| DE | 10 2018 206 758 | 11/2019 |
| EP | 0 930 086 | 7/1999 |
| EP | 2 752 209 | 7/2014 |
| EP | 2 782 210 | 9/2014 |
| EP | 2 859 911 | 4/2015 |
| EP | 2 966 753 | 1/2016 |
| EP | 2 454 799 | 9/2016 |
| EP | 2 709 689 | 4/2017 |
| EP | 3 220 505 | 9/2017 |
| EP | 3 423 126 | 2/2021 |
| EP | 3 198 677 | 3/2021 |
| EP | 3 248 647 | 3/2021 |
| EP | 3 436 106 | 3/2021 |
| EP | 3 436 105 | 4/2021 |
| EP | 3 116 407 | 5/2021 |
| EP | 2 608 731 | 7/2021 |
| EP | 3 077 018 | 10/2021 |
| EP | 3 485 936 | 10/2021 |
| EP | 3 539 613 | 2/2022 |
| EP | 2 858 718 | 3/2022 |
| EP | 3 624 867 | 3/2022 |
| EP | 3 755 237 | 4/2022 |
| EP | 3 485 819 | 9/2022 |
| EP | 3 808 408 | 11/2022 |
| EP | 3 858 422 | 11/2022 |
| EP | 2 892 583 | 1/2023 |
| EP | 3 597 231 | 1/2023 |
| EP | 3 856 275 | 1/2023 |
| EP | 3 003 420 | 2/2023 |
| EP | 3 946 511 | 4/2023 |
| JP | 2013-013216 | 1/2013 |
| JP | 2018-046708 | 3/2018 |
| WO | WO 2008/106103 | 9/2008 |
| WO | WO 2009/023905 | 2/2009 |
| WO | WO 2009/029977 | 3/2009 |
| WO | WO 2010/042054 | 4/2010 |
| WO | WO 2011/007300 | 1/2011 |
| WO | WO 2012/147061 | 11/2012 |
| WO | WO 2015/152732 | 10/2015 |
| WO | WO 2017/021846 | 2/2017 |
| WO | WO 2017/060257 | 4/2017 |
| WO | WO 2017/066257 | 4/2017 |
| WO | WO 2017/089440 | 6/2017 |
| WO | WO 2017/118738 | 7/2017 |
| WO | WO 2017/165372 | 9/2017 |
| WO | WO 2017/218349 | 12/2017 |
| WO | WO 2018/033799 | 2/2018 |
| WO | WO 2018/100192 | 6/2018 |
| WO | WO 2019/025258 | 2/2019 |
| WO | WO 2019/025259 | 2/2019 |
| WO | WO 2019/025260 | 2/2019 |
| WO | WO 2019/101786 | 5/2019 |
| WO | WO 2019/145253 | 8/2019 |

(56) References Cited

FOREIGN PATENT DOCUMENTS

| WO | WO 2019/158996 | 8/2019 |
|----|----------------|--------|
| WO | WO 2019/183247 | 9/2019 |
| WO | WO 2019/185511 | 10/2019 |
| WO | WO 2019/185512 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/229224 | 12/2019 |
| WO | WO 2019/234151 | 12/2019 |
| WO | WO 2019/241556 | 12/2019 |
| WO | WO 2019/244031 | 12/2019 |
| WO | WO 2020/089429 | 5/2020 |
| WO | WO 2023/076869 | 5/2023 |

OTHER PUBLICATIONS

International Preliminary Report on Patentability and Written Opinion received in PCT/EP2019/061294, dated Aug. 24, 2020 in 12 pages.

\* cited by examiner

WIRELESS ENERGY TRANSFER SYSTEM WITH FAULT DETECTION

BACKGROUND

Field

The present invention relates to an energy transfer system having a transmitter unit and a receiver unit for the wireless transfer of energy, a method for the wireless transfer of energy, and a computer program for the implementation thereof.

Description of the Related Art

A wireless, in particular inductive, transfer of energy can be used to supply energy to consumers and in particular to charge energy stores. In this type of energy transfer, a magnetic field can be generated in a transmitter unit having a primary coil, which induces a voltage and thus a current flow in a receiver unit having a secondary coil.

SUMMARY

This type of energy transfer can in particular be used for so-called transcutaneous energy transfer, in which the receiver unit is placed or implanted under the skin in a human or animal body. Such a transcutaneous energy transfer is advantageous in circulatory or cardiac support systems (so-called VAD systems, ventricular assist devices), for example, since there is then no permanent wound in the skin through which a wire is routed.

A crucial factor for this transcutaneous transfer of energy is that any critical states or faults in the system, in particular in the receiver unit placed or implanted in the body, are detected, so that an appropriate fault response can be initiated. The concepts for fault detection and fault response should furthermore be as secure as possible against tampering or attacks from the outside. This is in no small part due to the high approval standards for medical devices. It must generally also be possible to handle any time-critical faults within as short a reaction time as possible.

Since there is no wired connection for such a wireless transfer of energy, there is no direct communication path for fault detection or fault response. It is therefore customary to implement a wireless communication link between the two subsystems transmitter unit and receiver unit. In the case of transcutaneous energy transfer in particular, concepts such as infrared communication or classic approaches using radio technology, as described for example in EP 0 930 086 A1 (keyword: shielding, vulnerability), often reach their limits.

Implementing communication by modulating a data signal onto the energy transfer path, as described for example in US 2013/0260676 A1, is known as well. US 2017/0093218 A1 proposes a modulation strategy by varying the switching times of the synchronous rectifier.

These communication strategies are also suitable for generating error messages, but entail delays due to protocol-specific overhead, which can be problematic especially in particularly time-critical faults such as overvoltage.

For time-critical faults, therefore, recourse is often taken to hardware protection devices that can catch faults by connecting an additional hardware unit, as proposed in US 2016/0254659 A1 for example.

Based on this, the underlying object of the invention is to further improve the systems and methods for wireless transfer of energy known in the state of the art and quickly detect time-critical faults and take appropriate countermeasures, if possible without complex hardware.

To achieve this object, an energy transfer system and a method for wireless transfer of energy, as well as a computer program for the implementation thereof are described herein. Advantageous configurations and further developments are also described herein.

The invention is based upon an energy transfer system for the wireless transfer of energy having a transmitter unit and a receiver unit separate from the transmitter unit. The transmitter unit comprises a primary coil, which can be supplied with a supply voltage. To produce an oscillation of the voltage in the primary coil with a supply voltage present as a DC voltage, an inverter, for example with suitable semiconductor switches, is therefore usually provided as well. An alternating magnetic field can thus be produced by means of the transmitter unit.

The receiver unit correspondingly comprises a secondary coil, to which an energy sink, such as an energy store and/or a consumer, and in particular also an intermediate circuit capacitor or generally an intermediate circuit capacitance, is connected via a rectifier. The rectifier can in particular be a passive rectifier having suitable diodes. However, an active rectifier having suitable semiconductor switches, for example, is advantageous as well. The intermediate circuit capacitor, which is charged during energy transfer, serves in particular to smooth the alternating voltage that is induced in the secondary coil and then rectified. This type of wireless energy transfer is therefore, as already mentioned above, an inductive transfer of energy.

An energy store as the energy sink, for example an accumulator or a rechargeable battery, which is connected to the rectifier, can or should thereby be charged by means of the wireless or inductive transfer of energy. To apply an appropriate voltage to the energy store and provide a suitable current flow, a suitable circuit, such as a buck converter, is preferably provided.

Additionally or alternatively, a consumer can also be connected to the rectifier as the energy sink, for example, which is supplied with voltage and thus with energy using the intermediate circuit voltage in the intermediate circuit or at the intermediate circuit capacitor.

According to the invention, it is now provided that the receiver unit is configured to detect a fault in an energy flow from the secondary coil to the energy sink and, if a fault has been detected, carry out a fault mode with at least one operating parameter of the receiver unit preferably in a range outside the given specification. The transmitter unit is furthermore configured to recognize the fault mode of the receiver unit, in particular by means of a plausibility check of a system state, and, if the fault mode of the receiver unit has been recognized, carry out a fault response.

For this purpose, the transmitter unit is in particular configured to perform a continuous or repeated monitoring to recognize the fault mode. The aforementioned fault response can in particular be an emergency shutdown, in which the transfer of energy is switched off or terminated, for example quickly and purposefully, which is associated with a termination of the energy supply in the receiver unit.

For this purpose, in addition to the energy sink, the receiver unit can comprise a suitable sensor system or means for controlling the power flow or the energy flow from the secondary coil to the energy sink. For example, a voltage sensor or a voltage measuring device for detecting an overvoltage in the receiver unit can be provided. In other words, the receiver unit is preferably configured to record a voltage at the energy sink or directly at an intermediate circuit downstream of the rectifier (the voltage at the intermediate circuit downstream of the rectifier can differ from the voltage directly at the energy sink) and to detect the fault based on an exceedance of a threshold value of the recorded voltage. The receiver unit is in particular also configured to perform a continuous or repeated monitoring to detect the fault. A measurement of the voltage directly at the intermediate circuit or there at an intermediate circuit capacitor downstream of the rectifier is particularly advantageous.

If a fault, i.e. an overvoltage, is detected, the aforementioned fault mode is carried out. This is in particular an adjustment of an operating point of the system, i.e. the receiver unit, such that the system is outside the specification range. Such a specification range is in particular a predetermined or defined range for operating parameters such as voltage and current in the receiver unit, within which proper operation of the receiver unit can be ensured or is at least intended.

The fault mode can be carried out by, in particular briefly, increasing a current power beyond the maximum specified power or within the given specification, for example. For example, the receiver unit is configured to set the fault mode by increasing an output power of the receiver unit and/or an output current for the energy sink as the at least one operating parameter. In particular, the charging current for an energy sink configured as a battery is increased. Such a brief increase in power should actually briefly charge the battery at a higher rate. Assuming that any capacitances in the receiver unit are small relative to the power or energy flow, the change in the operating point in the transmitter unit can be detected or recognized very quickly.

With suitable means in the transmitter unit or an appropriate sensor system for detecting the system state, i.e. the state of the transmitter unit, for example to record or measure an input power of the primary coil, the fault can be detected very quickly, in particular by means of a plausibility check. Because the power flows from the transmitter unit to the receiver unit, the fault mode implemented or carried out in the receiver unit, e.g. by increasing the charging current and thus the output power of the receiver unit, is apparent in the transmitter unit, e.g. by increased power demand outside the specification range at the input of the transmitter unit. The increased power demand can be detected by an appropriate sensor system for measuring the input power of the transmitter unit, for example, e.g. by measuring the supply voltage and the current of the transmitter unit within the same, by means of which a fault can be inferred. Depending on the selected topology, individual states in the transmitter unit contain more or less information about the current operating state of the receiver unit and are thus more or less suitable for detecting the fault mode provoked in the receiver unit. Thus, for the embodiment described in more detail in the following, if the supply voltage of the transmitter unit is constant, a measurement of the input current of the transmitter unit would be sufficient to detect the required input power.

Such a plausibility check can in particular be carried out online or in real time. Different faults can thus be assigned to defined system states that do not occur during normal operation. When the fault occurs, the system is deliberately forced into the defined system state, which does not occur in normal operation, in order to communicate specific faults from the receiver unit to the transmitter unit. It should be noted that different systems also allow different degrees of freedom (e.g. the ability to briefly increase the output power).

Because of the indirect communication about the system state or the power or energy flow, the proposed concept is difficult for external attackers to disrupt. A large amount of energy would be required to significantly affect the system, in particular the receiver unit. Classic jammers cannot be used here. Recording the system state is also much more dynamic than a classic modulation of the power flow (e.g. via frequency modulation). Although such methods are well-suited for sending error messages, as mentioned at the outset, they are generally based on a specific protocol that often incurs some overhead, which can cause problems in time-critical situations. A considerable amount of additional effort (e.g. more development effort, use of a hardware modulator, etc.) is also usually required there. The proposed energy transfer system, on the other hand, requires no additional hardware. In a suitable system, the fault detection can be implemented simply by adapting the software.

Although the presented energy transfer system with a transmitter unit and a receiver unit is advantageous for any type of wireless or inductive energy transfer, is it nevertheless particularly useful if the receiver unit is configured to be placed underneath the skin of a human or animal body, in particular implanted, and/or if the transmitter unit is configured to be placed on the skin outside a human or animal body. The energy transfer system is thus used for the aforementioned transcutaneous energy transfer. The mentioned advantages come into play particularly clearly here, because, as mentioned, an energy transfer that is particularly tamper-proof or protected against external attacks is desired or required.

A further object of the invention is a method for the wireless transfer of energy with a transmitter unit and a receiver unit separate from the transmitter unit, which transmitter unit comprises a primary coil which can be supplied with a supply voltage, and which receiver unit comprises a secondary coil to which an energy sink is connected via a rectifier. Monitoring for a fault in an energy flow from the secondary coil to the energy sink is performed in the receiver unit and, if a fault is detected, a fault mode of the receiver unit is carried out with at least one operating parameter of the receiver unit, preferably in a range outside the given operating specification, so that the fault mode is clearly distinguishable from normal operation. Monitoring for the fault mode of the receiver unit is performed in the transmitter unit and, if the fault mode is recognized in the transmitter unit, a fault response is carried out by the transmitter unit.

The fault mode of the receiver unit is advantageously recognized via an increased input power in the transmitter unit.

With regard to the advantages and further configurations of the method, reference is made to the above statements pertaining to the energy transfer system according to the invention, which apply here accordingly.

The implementation of the method in the form of a computer program is advantageous too, because, in particular if an executing control device is also used for other tasks and is therefore already available, the associated costs are very low. Suitable data carriers for providing the computer program are in particular magnetic, optical and electrical memories, such as hard drives, flash memory, EEPROMs, DVDs, etc. It is also possible to download a program via computer networks (internet, intranet, etc.).

Further advantages and configurations of the invention will emerge from the following description and the accompanying drawing.

BRIEF DESCRIPTION OF THE DRAWINGS

The invention is schematically illustrated in the drawing based on a design example and is described in the following with reference to the drawing.

DETAILED DESCRIPTION

Figure 1:
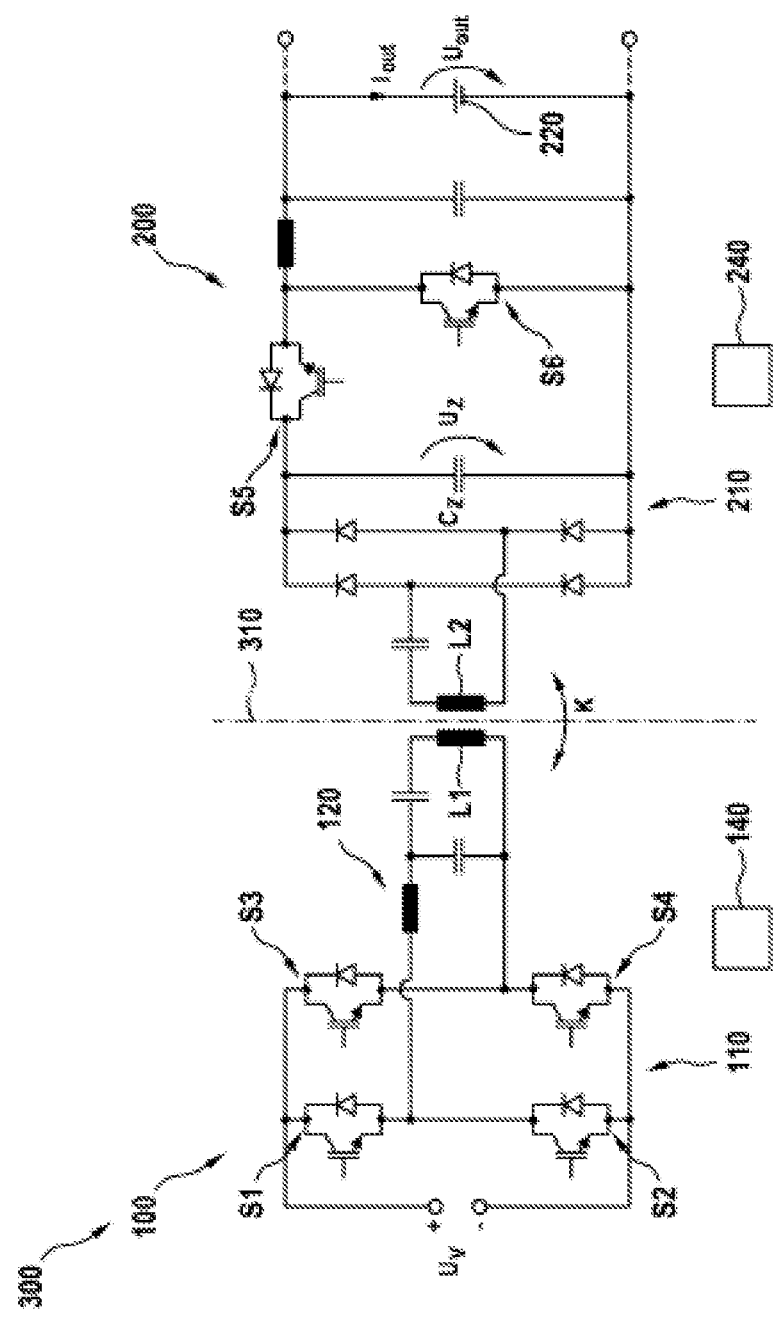
FIG. 1 schematically shows an energy transfer system according to the invention in a preferred embodiment.

FIG. 1 schematically illustrates an energy transfer system 300 according to the invention for the wireless transfer of energy in a preferred embodiment. The energy transfer system comprises a transmitter unit 100 and a receiver unit 200 which is separate from said transmitter unit, each according to a preferred embodiment of the invention.

The transmitter unit 100 comprises a primary coil $L_1$, to which a supply voltage $U_V$ can be applied via an inverter 110 comprising four semiconductor switches, for example MOSFETs or bipolar transistors, labeled $S_1$ to $S_4$. In addition, a prefilter 120 comprising unspecified components and a compensation capacitance are connected between the inverter 110 and the primary coil $L_1$. In the case of resonant actuation (actuation with the design frequency), the compensation capacitance serves as a reactive power compensation.

Therefore, when the supply voltage $U_V$ is applied and the inverter 110 is appropriately actuated, an alternating magnetic field can be produced by means of the coil $L_1$.

A computing unit 140 is integrated into the transmitter unit 100.

The receiver unit 200 comprises a secondary coil $L_2$ to which an intermediate circuit capacitor $C_Z$ is connected via a compensation capacitance and a rectifier 210. An energy storage unit 220 is then connected as an energy sink to the intermediate circuit capacitor $C_Z$ by means of two semiconductor switches $S_5$ and $S_6$, which can be configured as MOSFETs or bipolar transistors, for example, and, together with an inductance and a capacitance, serve in particular as a buck converter. A consumer can be connected via the indicated connections, for example.

The rectifier 210 is configured as a passive rectifier with four unspecified diodes. However, it is also advantageous to use an active rectifier, for example with semiconductor switches. The energy storage unit 220 can in particular be an accumulator or a rechargeable battery.

The receiver unit 200 can now in particular be configured to be placed or implanted under skin, indicated here with 310, and used for a circulatory or cardiac support system, for example. The energy storage unit 220 can in particular be used to supply energy to such a circulatory or cardiac support system.

With the transmitter unit 100 correspondingly positioned outside or on the skin 310, and with appropriate positioning, a coupling between the primary coil $L_1$ of the transmitter unit 100 and the secondary coil $L_2$ of the receiver unit 200 is achieved. This coupling is described with a coupling factor K.

If the transmitter unit 100 is now actuated or operated such that an alternating magnetic field is produced by means of the primary coil $L_1$, the coupling induces a voltage or a current flow in the secondary coil $L_2$. This in turn causes the intermediate circuit capacitor $C_Z$ to be charged, so that a voltage $U_Z$ is present there.

The supply voltage $U_V$ (also referred to as the input voltage) at the primary coil $L_1$ can be set as desired by phase shifting or phase control; i.e. the supply voltage can be adjusted.

An output voltage $U_{out}$ with an output current $I_{out}$ can be set at the energy store using the buck converter mentioned above. The output current $I_{out}$ thus corresponds to a charging current for the energy store.

For the energy transfer system 300 shown, in the case of the selected topology (parallel compensation in the transmitter unit and serial compensation in the receiver unit), a steady-state relationship for the intermediate circuit voltage $U_Z$ as a function of various already mentioned variables can be described as follows:

$$\frac{U_Z}{U_V} = \frac{K}{A}\sqrt{\frac{L_2}{L_1}}.$$

A specifies a determinable or predeterminable design parameter of the prefilter or voltage divider 120 in the transmitter unit 100. It can be seen that the coupling factor K goes into a stationary transfer function linearly. The intermediate circuit voltage $U_Z$ is therefore strongly dependent on the relative positioning of the transmitter unit 100 and the receiver unit 200, or their coils $L_1$ and $L_2$, to one another.

In the case of a transcutaneous energy transfer, the coupling factor K can sometimes vary by a factor of up to ten (for example due to shifting of the extracorporeal system, i.e. the transmitter unit, as a result of a fall, or strong pressure from incorrect positioning during sleep). Designing the intracorporeal system, i.e. the transmitter unit, for such a wide voltage range would result in a great deal of additional effort and increased losses.

For this reason, a critical increase in the intermediate circuit voltage $U_Z$ is detected and the supply voltage $U_V$ is adjusted accordingly. However, since the supply voltage UV is usually set extracorporeally by phase shifting or phase control, a critical increase in the intracorporeal voltage or the intermediate circuit voltage $U_Z$ on the extracorporeal side cannot readily be detected.

In the context of the invention, therefore, an impermissible increase in the intermediate circuit voltage $U_Z$ on the intracorporeal side is detected by means of a voltage measurement. This can, for example, be carried out by a computing unit 240 integrated into the receiver unit 200 and comprising a not-depicted voltage measuring device. The operating point is then shifted out of the specification range by intracorporeally increasing the output power of the system by a rapid upregulation or an increase in the charging current for the energy store, i.e. the output current $I_{out}$. This can be done by appropriately actuating the buck converter which is operated in a current-regulated manner by means of the computing or control unit 240. A fault mode is therefore set purposefully.

On the extracorporeal side, an online plausibility check is carried out continuously (i.e. in real time) by monitoring the input power of the transmitter unit and, if necessary, comparing it to an efficiency-adjusted output power of the receiver unit. It is also conceivable for intracorporeally determined values of the output power to be communicated to the extracorporeal computing unit 140 without this being time-critical. The change in the system state, i.e. the fault mode, is immediately detected by this plausibility check, and an emergency shutdown is initiated as a fault response. This recognition of the fault mode or the plausibility check can, for example, be carried out by the computing unit 140 integrated into the transmitter unit 100.

The threshold of the input power at which an emergency shutdown is performed can be selected more precisely, the more information is known about the system state. The current target operating point of the system, the efficiency and the coupling factor, for example, can be included in the plausibility check.

Figure 2:
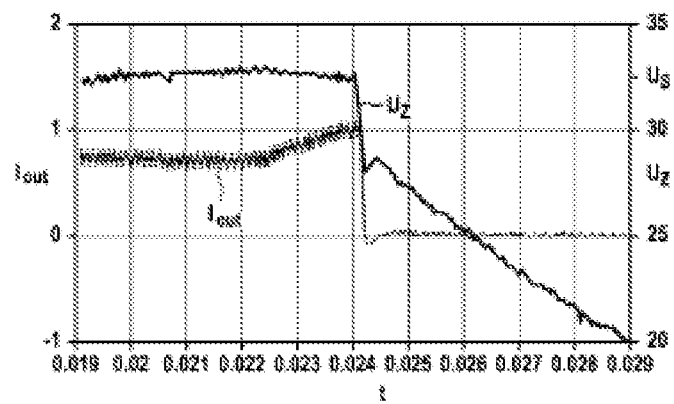
FIG. 2 shows a progression of the intermediate circuit voltage and the output current when using an energy transfer system according to the invention in a preferred embodiment.

FIG. 2 shows a progression of the intermediate circuit voltage and the output current when using an energy transfer system according to the invention in a preferred embodiment (or when carrying out a corresponding method). For this purpose, an output current $I_{out}$ in A and an intermediate circuit voltage $U_Z$ in V, as discussed with reference to FIG. 1, are plotted over the time t in s.

As soon as the intermediate circuit voltage $U_Z$ exceeds a critical value, i.e. a threshold value, which is labeled here as Us (there is therefore an overvoltage in the energy flow from the secondary coil to the energy store), the output current $I_{out}$ is increased at a constant output voltage at the energy store, which means an increase in the output power beyond the specified or required operating point. A fault mode is therefore carried out purposefully.

This increase in output power is recognized or detected extracorporeally, i.e. in the transmitter unit. It can be seen that the intermediate circuit voltage $U_Z$ drops after the emergency shutdown. The entire process from exceeding the critical voltage limit or the threshold value Us to the drop in the output current $I_{out}$ takes about 1.5 ms for the described example, but can still be reduced significantly, for example by reducing the system-internal energy store or increasing an available control reserve.

In particular for the energy transfer device 300 shown in FIG. 1, there are also other advantages. Due to ohmic components in the receiver unit 200, an increase in the output power already automatically leads to a reduction in the intermediate circuit voltage $U_Z$ as can also be seen in FIG. 2. The intermediate circuit voltage $U_Z$ therefore already drops before the transfer of energy is terminated by the transmitter unit.

If the increase in the intermediate circuit voltage $U_Z$ has a smaller time constant than the response time of the current regulator for the output current $I_{out}$, the output current $I_{out}$ and thus the output power will increase solely as a result of the system behavior of the buck converter. This, too, leads to a shutdown by the transmitter unit.

Figure 3:
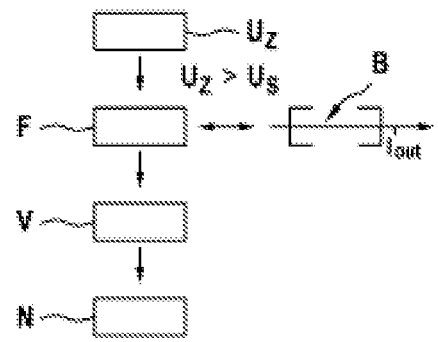
FIG. 3 shows a sequence of a method according to the invention in a preferred embodiment.

FIG. 3 schematically shows a sequence of a method according to the invention in a preferred embodiment or the steps that take place in a corresponding energy transfer system from top to bottom.

The intermediate circuit voltage $U_Z$ is monitored. As soon as this intermediate circuit voltage $U_Z$ exceeds the threshold value $U_s$, a fault mode F is carried out, namely by setting the output current or charging current $I_{out}$ as the operating parameter of the receiver unit to a value from a range outside the given specification B.

This fault mode is recognized via a comparison V of the input and the output power and/or via a comparison of the input power with a specified maximum input power as a fixed or given threshold value in the transmitter unit and an emergency shutdown N is carried out as a fault response.

The invention claimed is:

1. A transcutaneous energy transfer system for wireless transfer of energy, the transcutaneous energy transfer system comprising:
   a transmitter unit comprising a primary coil configured to receive a supply voltage, the transmitter unit configured to be placed on skin outside of a human or animal body and transcutaneously transmit energy; and
   a receiver unit comprising a secondary coil connected to an energy sink via a rectifier, a control unit, and a step-down converter, the receiver unit configured to be placed underneath the skin in the human or animal body and receive the energy transcutaneously transmitted by the transmitter unit, wherein the receiver unit is configured to detect a fault in energy flow from the secondary coil to the energy sink when an operating parameter of the receiver unit is outside of a specification range, wherein the energy sink comprises an energy store configured to supply energy to a cardiac support system, and wherein the energy store comprises an accumulator or a rechargeable battery;
   wherein the control unit of the receiver unit is configured to actuate the step-down converter to perform a fault mode in response to detecting the fault by stepping down a voltage received at the secondary coil at the step-down converter and increasing a charging current for the accumulator or the rechargeable battery; and
   wherein the transmitter unit is configured to:
      detect the fault mode of the receiver unit based at least in part on an input power of the primary coil; and
      perform a fault response by initiating an emergency shutdown of the transcutaneous transmission of energy to the receiver unit in response to detecting the fault mode of the receiver unit.

2. The transcutaneous energy transfer system of claim 1, wherein the transmitter unit is configured to detect the fault mode of the receiver unit based at least in part on a comparison of the input power of the primary coil with an output power or a predetermined threshold value.

3. The transcutaneous energy transfer system of claim 1, wherein the transmitter unit is configured to detect the fault mode of the receiver unit by performing a plausibility check of a system state.

4. The transcutaneous energy transfer system of claim 3, wherein the system state comprises a current target operating point of the transcutaneous energy transfer system, an efficiency of the transcutaneous energy transfer system, and a coupling factor between the primary coil of the transmitter unit and the secondary coil of the receiver unit.

5. The transcutaneous energy transfer system of claim 1, wherein the transmitter unit is configured to continuously or repeatedly monitor for the fault mode of the receiver unit.

6. The transcutaneous energy transfer system of claim 1, wherein an intermediate circuit capacitor is connected to the secondary coil via the rectifier, and wherein the receiver unit is configured to determine a voltage at the energy sink or at the intermediate circuit capacitor and detect the fault when the voltage at the energy sink or at the intermediate circuit capacitor exceeds a threshold value.

7. The transcutaneous energy transfer system of claim 1, wherein the receiver unit is configured to perform the fault mode by changing at least one operating parameter to be outside of a given specification range of the operating parameter.

8. The transcutaneous energy transfer system of claim 1, wherein the receiver unit continuously or repeatedly monitors for the fault.

9. The transcutaneous energy transfer system of claim 1, wherein the transmitter unit comprises an inverter configured to produce an oscillation of the supply voltage.

10. The transcutaneous energy transfer system of claim 1, wherein the receiver unit comprises a sensor system configured to control energy flow from the secondary coil to the energy sink.

11. The transcutaneous energy transfer system of claim 1, wherein the energy sink comprises a buck converter.

12. The transcutaneous energy transfer system of claim 1, wherein the rectifier comprises a passive rectifier with diodes.

13. The transcutaneous energy transfer system of claim 1, wherein the rectifier comprises an active rectifier with semiconductor switches.

14. A method for transcutaneous wireless transfer of energy, the method comprising:
  detecting, by a receiver unit placed underneath skin in a human or animal body and comprising a secondary coil connected to an energy sink via a rectifier, the energy sink comprising an energy store comprising an accumulator or a rechargeable battery configured to supply energy to a cardiac support system, a fault in energy flow from the secondary coil to the energy sink;
  performing, by a control unit of the receiver unit, a fault mode in response to detecting the fault by increasing a charging current for the accumulator or the rechargeable battery, wherein the fault mode is performed by the control unit actuating a step-down converter to step down a voltage received at the secondary coil at the step-down converter;
  detecting the fault mode by a transmitter unit placed on the skin outside of the human or animal body, the transmitter unit comprising a primary coil configured to be supplied with a supply voltage; and
  performing, by the transmitter unit, a fault response by initiating an emergency shutdown of a transcutaneous transfer of energy to the receiver unit in response to detecting the fault mode.

15. The method according to claim 14, wherein the fault mode of the receiver unit is performed by changing at least one operating parameter of the receiver unit to be outside of a specification range of the respective operating parameter.

16. The method according to claim 14, wherein the fault is detected when an operating parameter of the receiver unit is outside a specification range, and the fault mode is detected based at least in part on an input power of the primary coil.

17. A computer-readable storage medium storing therein computer-readable instructions that, when executed by a processor conducting a transcutaneous wireless energy transfer, causes the processor to:
  detect, by a receiver unit placed underneath skin in a human or animal body and comprising a secondary coil connected to an energy sink via a rectifier, the energy sink comprising an energy store comprising an accumulator or a rechargeable battery configured to supply energy to a cardiac support system, a fault in energy flow from the secondary coil to the energy sink;
  perform, by a control unit of the receiver unit, a fault mode in response to detecting the fault by increasing a charging current for the accumulator or the rechargeable battery, wherein the fault mode is performed by the control unit stepping down a voltage received at the secondary coil at a step-down converter;
  detect the fault mode by a transmitter unit placed on the skin outside of the human or animal body, the transmitter unit comprising a primary coil configured to be supplied with a supply voltage; and
  perform, by the transmitter unit, a fault response by initiating an emergency shutdown of a transcutaneous transfer of energy to the receiver unit in response to the transmitter unit detecting the fault mode.

18. The method according to claim 14, wherein the transmitter unit continuously or repeatedly monitors for the fault mode of the receiver unit.

19. The method according to claim 14, wherein the receiver unit continuously or repeatedly monitors for the fault.

* * * * *